United States Patent
Benderev

Patent Number: 6,030,338
Date of Patent: Feb. 29, 2000

[54] EXTERNAL VIBRATORY EXERCISING DEVICE FOR PELVIC MUSCLES

[76] Inventor: Theodore V. Benderev, 26975 Magnolia Ct., Laguna Hills, Calif. 92653

[21] Appl. No.: 09/078,937

[22] Filed: May 14, 1998

Related U.S. Application Data

[63] Continuation-in-part of application No. 08/558,642, Nov. 13, 1995, Pat. No. 5,782,745.

[51] Int. Cl.[7] .................................................. A61F 2/00
[52] U.S. Cl. ................................. 600/30; 128/DIG. 25; 128/885
[58] Field of Search ........................ 600/29–32; 128/885, 128/DIG. 25

[56] References Cited

U.S. PATENT DOCUMENTS

| | | | |
|---|---|---|---|
| 4,198,979 | 4/1980 | Cooney et al. | 128/295 |
| 4,246,901 | 1/1981 | Michaud | 128/295 |
| 4,681,572 | 7/1987 | Tokarz et al. | 604/329 |
| 4,749,186 | 6/1988 | Harding-Randle | 128/DIG. 25 |
| 4,889,533 | 12/1989 | Beecher | 604/330 |
| 5,437,649 | 8/1995 | Letchworth | 604/278 |
| 5,483,976 | 1/1996 | McLaughlin et al. | 128/665 |
| 5,513,660 | 5/1996 | Simon et al. | 128/885 |
| 5,603,685 | 2/1997 | Tutrone, Jr. | 600/29 |
| 5,611,768 | 3/1997 | Tutrone, Jr. | 600/29 |
| 5,782,745 | 7/1998 | Benderev | 128/DIG. 25 |

*Primary Examiner*—John P. Lacyk
*Attorney, Agent, or Firm*—Stetina Brunda Garred & Brucker

[57] ABSTRACT

A device and method for treating urinary as well as fecal incontinence by using proprioceptive neuromuscular facilitation. The device is adapted to be compressively positioned against the crotch of the user to thus identify target pelvic floor muscles and muscle groups responsible for urinary and/or fecal continence and provide periodic stimulus thereto by way of pressure, stretching, resistance, vibration, and/or heat. The frequency, duration, and extent of the stimulus may be varied as desired for exercise regimens.

9 Claims, 2 Drawing Sheets

Fig. 4
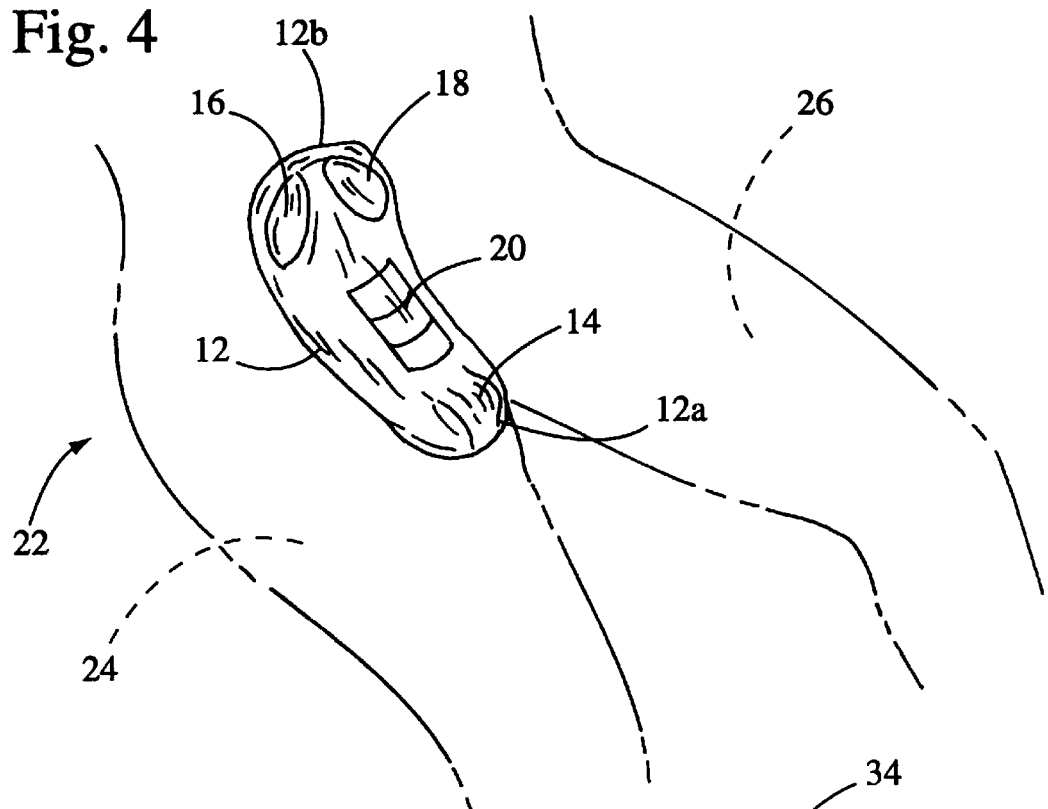
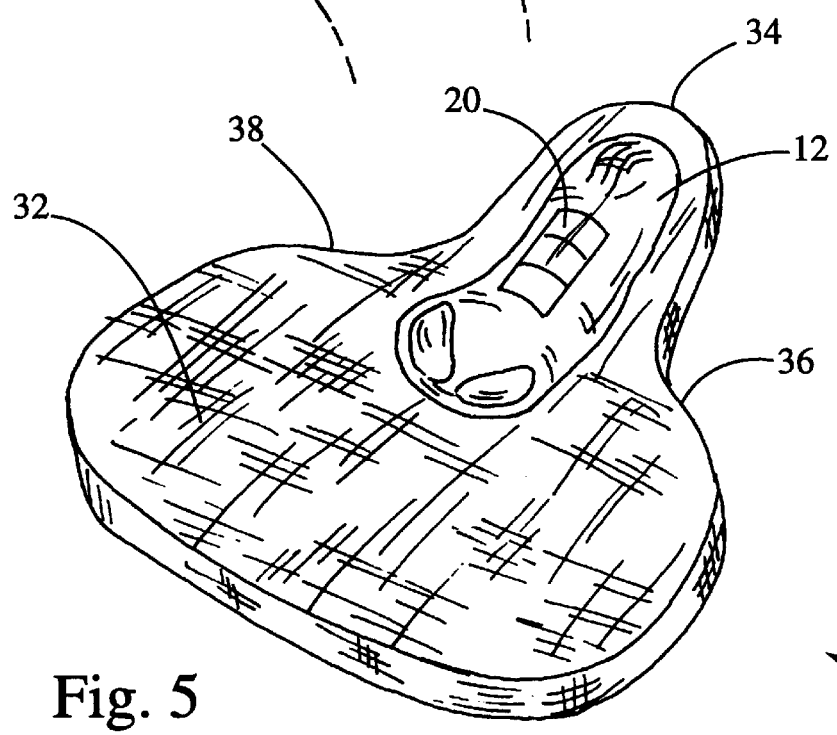
Fig. 5

EXTERNAL VIBRATORY EXERCISING DEVICE FOR PELVIC MUSCLES

RELATED APPLICATION

The present application is a continuation-in-part of U.S. patent application Ser. No. 08/558,642 entitled DEVICES AND METHODS FOR ASSESSMENT AND TREATMENT OF URINARY AND FECAL INCONTINENCE, filed Nov. 13, 1995 now U.S. Pat. No. 5,782,745 and further relies on the disclosure made in Applicant's Disclosure Document, having a date of receipt of Jan. 16, 1998, Document No. not assigned.

FIELD OF THE INVENTION

The present invention relates generally to medical devices and methods, and more particularly, to devices and methods for facilitating the performance of pelvic muscle exercises.

BACKGROUND OF THE INVENTION

Urinary incontinence is believed to affect 15% to 30% of noninstitutionalized persons over the age of 60, and more then 50% of elderly persons (over the age of 60) who reside in nursing homes.

The presently available modes of treatment for urinary incontinence fall into four general categories, namely: i) management apparatus, ii) behavioral, iii) pharmacologic, and iv) surgical.

i. Management Apparatus For Incontinence

The management apparatus modes of treatment generally comprise absorbent and/or catheter structures worn by a user to retain any urinary and/or fecal incontinence. In their simplest forms, such devices comprise diaper-like structures which must be periodically changed by the user. Although such management apparatus has proven generally effective in masking the results of incontinence, they are uncomfortable to wear, difficult to change, and oftentimes fail during use thereby embarrassing the user.

ii. Behavioral Treatment For Incontinence

The use of behavioral training as a treatment for urinary and/or fecal incontinence can involve numerous behavioral techniques including; bladder re-training (e.g., voiding on a timed schedule), and/or the performance of exercises (e.g., Kegel exercises) to strengthen and retrain a group of muscles collectively known as the "pelvic floor muscles." As an adjunct to these behavioral training techniques, various intravaginal and/or intra-anal devices may be utilized to facilitate the performance of such pelvic muscle training exercises. Such intravaginal and/or intra-anal devices have included weighted apparatus such as intravaginal cones. Exemplary of such prior art include weighted cone devices such as the "FEMINA" cone manufactured by Dacomed Corporation, 1701 East 79th Street, Minneapolis, Minn., 55425. Other types of prior art devices include electromyographic (EMG) transducers or sensors which are insertable into or placed just outside of the vagina and/or anus to obtain EMG data indicative of baseline pelvic floor muscle tone and/or contraction(s) of the pelvic floor muscles during the performance of specific muscle contraction exercises. Such EMG data may be usable for diagnostic purposes as well as for monitoring the performance and/or effect of muscle training exercises. Some EMG devices have included means for providing visual or auditory feedback to assist the patient in the performance of pelvic floor muscle exercises (e.g., Myoexorciser III, available from Verimed 1401 East Broward Boulevard, Suite 200, Fort Lauderdale, Fla. 33301 and the PRS 8900 Office System made by Incare Medical Products, Libertyville, Ill. 60048.

Additionally, the prior art has included at least one transvaginal electrical stimulation device which is operative to deliver periodic or timed electrical stimulation to the pelvic floor muscles and nerves. Such electrical stimulation causes involuntary contraction of the pelvic floor muscles and may serve as an adjunct to the performance of volitional exercise and/or other behavioral training techniques (e.g., Microgyn II Stimulation Device, InCare Medical Products, Division of Hollister Incorporated, 2000 Hollister Drive, LibertyVille, Ill., 60048 and also the Innova Feminine Incontinence Treatment System available from EMPI, Inc., 1275 Grey Fox Road, St. Paul, Minn. 55112).

Although some of or all of the above-described devices and systems for exercise and/or training of the pelvic floor muscles may be effective in the treatment of urinary incontinence, there remains a need for the development of improved devices and systems which are capable of strengthening and training the pelvic floor muscles in minimal time, with minimal assistance from physicians or other health care professionals as well as a system which serves to remind a user to perform muscle exercises and to provide proprioceptive input to assist the user in exercising and strengthening desired muscles.

iii. Pharmacologic Treatment For Incontinence

The prior art pharmacologic treatment of urinary incontinence typically involves the long term administration of drugs. Such pharmacologic treatment may result in drug-related side effects. Also, the efficacy of such pharmacologic treatment is frequently limited and largely dependant upon the patient's ability or willingness to comply with the prescribed drug dosage schedule.

iv. Surgical Treatment For Incontinence

The prior art surgical modes of treatment of urinary incontinence typically involve the performance of one or more major surgeries procedures under anesthesia. These major surgical procedures can be associated with significant risks and may sometime result in post-surgical failure, infections, or other complications. Also, these surgical procedures typically result in significant expense to the patient and/or the patient's third party insurer.

As such, there exists a substantial need in the art for an incontinence treatment system and methodology which reduces or eliminates the need for prior art management apparatus and/or surgical treatments, reduces the use of long-term drug administration, accentuates muscle strengthening and training while reminding a patient to conduct muscle strengthening exercise, as well as provide a proprioceptive input to assist the patient in contracting the appropriate muscles and/or muscle groups necessary for the effective treatment of incontinence.

SUMMARY OF THE INVENTION

In accordance with the present invention, there is provided an external exercising device which is positionable upon the crotch of a patient to identify target muscle groups responsible for fecal and/or urinary continence and provide a signal to the patient to perform the appropriate muscle strengthening exercises therefor. The device generally comprises a saddle member having a signaling device housed therein, the latter being designed and configured to impart a perceptible stimulus against a portion of the crotch of the individual upon which the saddle member is positioned to thus remind the patient to perform the desired pelvic muscles strengthening exercises. The signaling device may preferably comprise a vibrator, pressure-exerting device, heater, or any other like device capable of generating a perceptible stimulus. A powersource, i.e., a battery, coupled to the signaling device and preferably housed within the saddle member is provided to drive the signaling device. Additionally, a timer apparatus may be mounted on or within the device to trigger and control the timing, duration, repetitions, and frequency of perceptible stimulus signals generated by the signaling device on a predetermined time schedule.

Still further in accordance with the invention, a remote controlled triggering device may be used in addition to, or in place of, a timer or other control apparatus mounted or housed within the saddle member. Such remote control apparatus may be utilized to trigger, control and/or schedule all operational parameters of stimulus produced by the signaling device from a remote location.

Still further in accordance with the invention, there is provided a method of treating urinary and/or fecal incontinence in a patient. In general, the method comprises the steps of compressively positioning an external exercising device of the forgoing character upon the crotch of a patient, and utilizing the device to intermittently deliver stretch, resistance, vibration, pressure or heat stimuli against the crotch and/or adjacent muscles thereabout to facilitate the performance of pelvic muscle strengthening exercises by the patient upon whom the device is positioned.

BRIEF DESCRIPTION OF THE DRAWINGS

These, as well as other features of the present invention, will become more apparent upon reference to the drawings, wherein:

FIG. 4 is a perspective view of the device depicted in FIG. 1 as aligned with and positioned upon the crotch of a patient, the latter is shown in phantom;

FIG. 5 is a perspective view of the external exercise device of the present invention as formed within a conventional seat cushion.

DETAILED DESCRIPTION OF THE PREFERRED EMBODIMENTS

The following detailed description and the accompanying drawings are provided for the purpose of describing certain presently preferred embodiments of the invention only, and are not intended to limit the scope of the claimed invention in any way.

Figure 1:
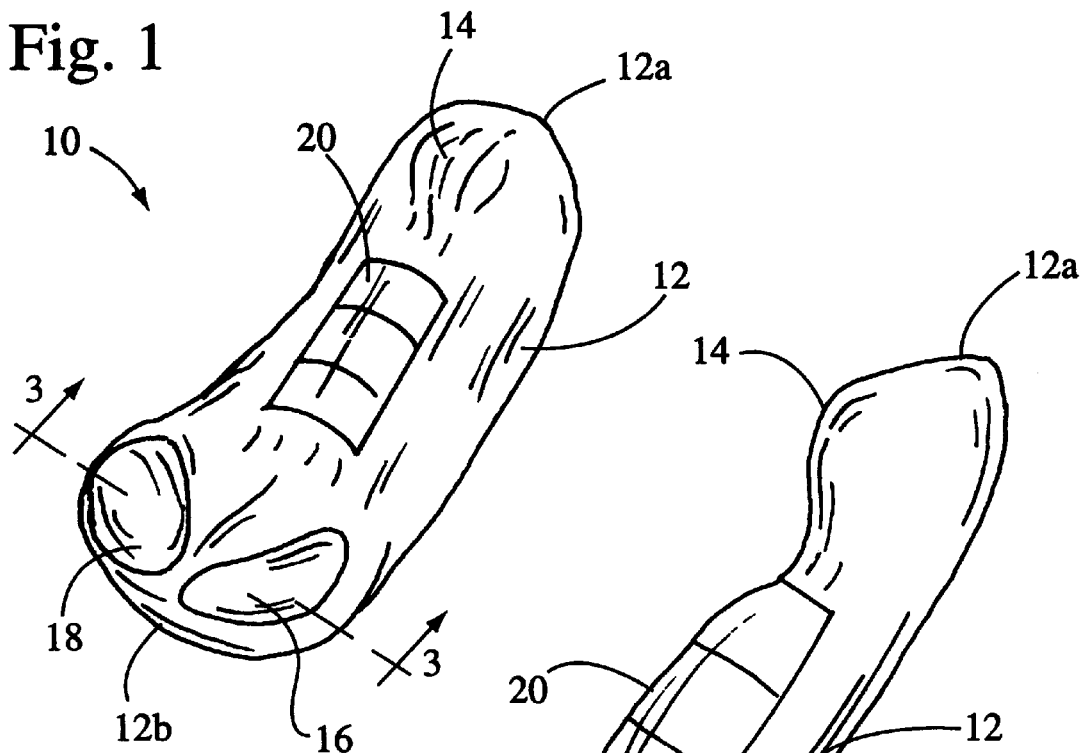
FIG. 1 is a perspective view of an external exercising device for facilitating the pelvic muscle strengthening exercises constructed in accordance to a preferred embodiment of the present invention.
Figure 3:
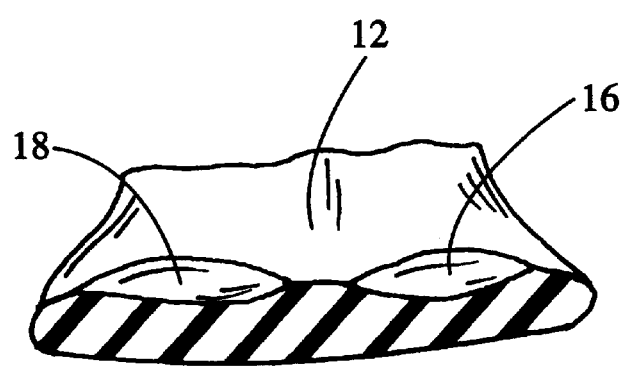
FIG. 3 is a cross-sectional view taken along the line 3—3 of FIG. 1.

Referring now to the drawings, and initially to FIG. 1, there is shown an external exercise device 10 constructed according to a preferred embodiment of the present invention. The device 10 is specifically designed to be utilized for the effective treatment of both urinary and fecal incontinence in females as well as male users or patients similar to those disclosed in pending parent application Ser. No. 08/558,642, the teachings of which are expressly incorporated herein by reference. As shown, the device 10 comprises an elongate saddle member 12 having an anterior end 12a and a posterior end 12b that is designed and configured to be compressively positioned against (i.e., straddled) the crotch of the user or patient. To accommodate and complement the anatomy of human beings, there is formed a cushioning member 14 upon the anterior end 12a of the saddle member 12, and a pair of opposed, generally oval-shaped recesses 16, 18 formed upon the posterior end 12b of the saddle member 12, the latter being more clearly depicted in FIG. 3.

As will be appreciated by those skilled in the art, cushion member 14 and recesses 16, 18 enable the saddle member 12 to adapt to the contours of the crotch between the respective inner thighs 24, 26 of the user or patient 22, as depicted in FIG. 4. In this regard, cushioning member 14 and recessed portions, 16, 18 are specifically designed and adapted to accommodate the user's skeletal structure of the pelvis when the patient is straddling the same in either a standing or sitting position.

Figure 2:
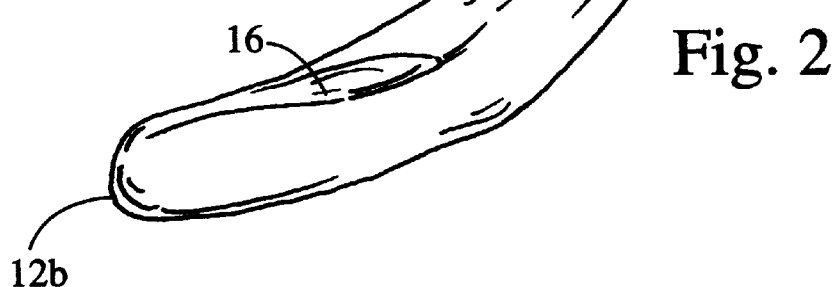
FIG. 2 is a side view of the device depicted in FIG. 1.

Housed within the saddle member 12 is a signaling device 20. As illustrated, the signaling device 20 is selectively positioned within the saddle member 12 such that a portion thereof is maintained in an upwardly-oriented configuration, as shown is FIG. 2, so that in use the stimulus generated thereby can be easily and directly perceived by the user/patient. The signaling device 20 is operative to provide timed or periodic changes in stimuli such as pressure, heat, and/or vibration to thus identify the target pelvic muscles/muscle groups responsible for fecal and/or urinary continence and promote proprioceptive neuromuscular facilitation and serve as a reminder to perform, and/or will facilitate the performance of, the appropriate muscle-strengthening exercises (e.g., Kegal exercises) by the patient upon whom the external exercise device 10 is positioned. A more detailed description of proprioceptive neuromuscular facilitation is found in Sullivan, P. E., et al.: "An Integrated Approach To Therapeutic Exercise", published by Reston Publishing Co., Reston, Va., pages 161–183, the disclosure of which is expressly incorporated herein by reference.

To enable the signaling device 20 to impart the stimulus to the patient to identify the target muscles and remind the patient to perform the pelvic muscle strengthening exercises therefor, a battery or powersource (not shown) is provided that is preferably housed within the saddle member 12. Additionally, a small triggering and control apparatus, such as the timer (not shown), may likewise be disposed within the saddle member 12 and connected to the signaling device 20 to cause the same to impart a stimulus to the patient on a predetermined time schedule. Alternatively, a remote control or telemetric switch or signal may be utilized to receive remote control signals and to schedule the operation of the device by actuating or de-actuating the signal device 20, as desired.

By virtue of the stimulus produced by the signaling device 20, the patient will sense the vibration, heat and/or exertion of pressure stretch or resistance against a portion of the perineum, vaginal, and/or anal wall and/or adjacent muscles thus identifying the target muscles or muscle groups sought to be strengthened. The patient will be thereby reminded and compelled to volitionally perform the prescribed pelvic floor muscle exercises. With respect to the incorporation of a pressure exerting mechanism, the pressure, stretch and/or resistance thereby created will thus improve the muscle-strengthening efficacy of such exercises by proprioceptive neuromuscular facilitation. After a predetermined time (e.g., sufficient time for the patient to perform the prescribed muscle exercise) has expired, or upon delivery of other triggering input (e.g., a remote control signal), the stimulus provided by the signaling device 20 is selectively terminated, i.e., the signaling device 20 is caused to assume a rest or non-operational mode.

After the signaling device 20 has returned to such "non-operative" mode, the device 10 may remain in such mode and continuously compressively engaged against the user's crotch, as depicted in FIG. 4. Upon expiration of a predetermined time period or upon receipt of a triggering input signal, the signaling device 20 will become actuated to thus assume its "operative" mode, whereby the device 10 will return to its stimulus-producing mode for an additional period of time.

The above-described sequence of events may be repeated on any prescribed schedule, or at any prescribed frequency or variable extension, so long as the device 10 remains sufficiently compressed against the patient. The patient will be thereby reminded and compelled to volitionally perform the prescribed pelvic wall muscle exercises of the identified pelvic floor muscles. Also, the vibration, heat, pressure, stretch and/or resistance created by the operatively positioned signaling device 20 will improve the muscle-strengthening efficacy of such exercises by proprioceptive neuromuscular facilitation.

As will be understood by those skilled in the art, as an alternative to transitioning between operative and non-operative modes whereby a stimulus is produced by the signaling device 20 at predetermined times, such device 20 may operate in a reverse manner whereby the device 20 is maintained in a continuously operative mode such that a first stimulus is continuously produced thereby. At predetermined times, such stimulus may be either increased or decreased to a degree such that the patient is provided with a perceptible change in the stimulus produced by the signaling device 20, which consequently serves to remind the patient to perform the prescribed pelvic floor muscle exercises.

Referring now to FIG. 5, there is shown the external exercise device of the present invention as disposed within a conventional seat member or cushion 30. Such seat cushion 30, which may take the form of a variety of designs well-known to those skilled in the art, is preferably provided with a generally planar area 32 to accommodate to the buttocks of the individual seated thereupon, and a protruding portion 34 flanked by recesses 36, 38 which thus defines an area upon which the individual may straddle. As illustrated, disposed within such portion 34 is the exercise device 10 with the signaling device 20 thereof being upwardly oriented and configured to aligned with and compress through the seat and against the crotch of the individual seated upon the seat member 30.

When an individual is seated thereupon, the device 10 of the of the present invention may be utilized to impart the necessary stimulus to the individual to thus identify the target muscle/muscle groups of the pelvic floor and remind the person to perform the pelvic muscle strengthening exercises therefor at predetermined times. As discussed above, the stimulus produced by the signaling device 20 may take the form of vibration, heat, and/or pressure. However, in the embodiment shown, it will be understood and appreciated that the stimulus produced by the signaling device 20 will be necessarily of a sufficient degree so as to be perceived by the individual seated upon the seat cushion 30, and more particularly the predetermined region of the person's anatomy resting thereupon (i.e, the crotch) to remind the user to perform the pelvic muscle strengthening exercises.

As will be appreciated by those skilled in the art, by incorporating the novel exercise device 10 of the present invention into such conventional seating devices 30 can thus eliminate the need to directly compress or otherwise mount the device 10 of the present invention directly upon the crotch or pelvic region of the user. Advantageously, such design enables those individuals in need of a strengthening exercise regimen to be provided with the necessary stimulus to adhere to such regimen, while simply remaining seated and thus free to do normal activities, such as work and the like.

It is to be understood that the individual elements and components of each above-described embodiment may be interchanged among and/or incorporated into any and all embodiments of the invention, even though certain elements or components may have been mentioned or described herein with respect certain embodiment(s) of the invention only.

It is to be further understood that various additions, deletions, modifications and alterations may be made to the above-described embodiments without departing from the intended spirit and scope of the present invention. Accordingly, it is intended that all such additions, deletions, modifications and alterations be included within the scope of the following claims.

What is claimed is:

1. A device for reminding a patient to perform pelvic muscle strengthening exercises comprising:
    a) a saddle member adapted to be positioned upon the pelvis of said patient; and
    b) a signaling device disposed within said saddle member for imparting, a perceptible stimulus to said patient at predetermined times to remind said patient to perform said pelvic muscle strengthening exercises.

2. The device of claim 1, wherein said saddle member comprises an elongate seat portion having an anterior end and a posterior end, said seat portion being designed and configured to be straddled by said patient.

3. The device of claim 1 wherein said signaling device comprises a vibrator designed to be alternately transitional between:
    i) a rest mode configuration wherein said vibrator is non-operative; and
    ii) a signal mode configuration wherein said vibrator is operative such that said perceptible stimulus is imparted thereby.

4. The device of claim 1 wherein said signaling device comprises a heater designed to be alternately transitional between:
    i) a rest mode configuration wherein said heater is non-operative; and
    ii) a signal mode configuration wherein said heater is operative such that said perceptible stimulus is imparted thereby.

5. The device of claim 1 wherein said signaling device comprises a pressure-exerting device designed to be alternately transitional between:
    i) a rest mode configuration wherein said signaling device exerts no more than a baseline pressure against a predetermined region of the patient's pelvis against which the signaling device is compressed; and
    ii) a signal mode configuration wherein said signaling device exerts more than the baseline pressure against the predetermined region of the patient's pelvis, said pressure exerted in said signal mode configuration being sufficient degree to produce a perceptible stimulus.

6. The device of claim 1 wherein said device further includes:

c) a timer apparatus disposed within said saddle member and coupled to said signaling device to selectively exert said perceptible stimulus at predetermined times.

7. The device of claim 1 wherein said device is adapted to be disposed within a conventional seat cushion.

8. The device of claim 1 wherein said signaling device is further designated and configured to compressively engage the pelvic floor muscles of said patient responsible for urinary continence and impart said perceptible stimulus thereto.

9. The device of claim 1 wherein said signaling device is further designed and configured to compressively engage the pelvic floor muscles of said patient responsible for fecal continence and impart said perceptible stimulus thereto.

* * * * *